United States Patent [19]

Columbus

[11] Patent Number: 5,055,203

[45] Date of Patent: Oct. 8, 1991

[54] BLOOD COLLECTION DEVICE WITH REDUCED SERUM DISPENSING VOLUME AND INTEGRAL NEEDLE

[75] Inventor: Richard L. Columbus, Rochester, N.Y.

[73] Assignee: Eastman Kodak Company, Rochester, N.Y.

[21] Appl. No.: 527,239

[22] Filed: May 22, 1990

[51] Int. Cl.$^5$ .......................................... B01D 21/26
[52] U.S. Cl. .................................. 210/741; 210/117; 210/136; 210/513; 210/518; 210/782; 422/101; 436/177; 494/2; 494/16; 604/411
[58] Field of Search ............ 210/741, 781, 782, 787, 210/789, 17, 130, 136, 514, 515, 516, 518, 380.1, 513; 422/101, 102; 436/177; 494/2, 16, 20, 21, 37; 604/403, 411, 413, 414

[56] References Cited

U.S. PATENT DOCUMENTS

| | | | |
|---|---|---|---|
| 2,954,769 | 10/1960 | Callahan et al. | 604/413 |
| 3,706,305 | 12/1972 | Berger et al. | 604/413 |
| 3,800,947 | 4/1974 | Smith | 210/117 |
| 3,965,889 | 6/1976 | Sachs | 210/789 |
| 4,012,325 | 3/1977 | Columbus | 210/516 |
| 4,136,036 | 1/1979 | Columbus | 210/516 |
| 4,788,154 | 11/1988 | Guigan | 210/787 |

*Primary Examiner*—W. Gary Jones
*Attorney, Agent, or Firm*—Dana M. Schmidt

[57] ABSTRACT

An integrated blood collection, separation and dispensing device is disclosed that allows a method of blood collection, serum separation and serum dispensing to occur using a single device (other than a centrifuge). The device preferably includes a transfer chamber for receiving separated serum, that has a three-dimensional shape that is reduced in volume and is configured to avoid air entrapment. A dispensing aperture in the transfer chamber fluidly connects the chamber with the atmosphere. Preferably, means are provided adjacent the dispensing aperture for generating a liquid pressure change indication of the presence of liquid advancing towards the dispensing aperture. A needle and a protective housing optionally are provided as an integral part of the device.

14 Claims, 7 Drawing Sheets

BLOOD COLLECTION DEVICE WITH REDUCED SERUM DISPENSING VOLUME AND INTEGRAL NEEDLE

FIELD OF THE INVENTION

The invention relates to phlebotomy devices used to collect whole blood and to separate serum therefrom, as well as to similar devices for collecting and separating phases of other multi-phase liquids.

BACKGROUND OF THE INVENTION

In the field of blood collection and separation, there has been no device which provides in one integrated article, the necessary components to first collect the blood, second do a phase separation to isolate plasma or serum, and third to dispense the serum. Instead, typically what has been done is, a syringe (device 1) collects the blood in a phlebotomy tube. This tube is then removed from the syringe, and either taken to a centrifuge, or poured off into a tube (device 2) to be spun in a centrifuge to achieve serum separation. Thereafter, the separated serum is then transferred to a container (device 3) that will allow dispensing of selected fractions of the serum.

More recently, device nos. 2 and 3 noted above have been combined into one device, as shown, for example, in U.S. Pat. No. 4,012,325. However, even that device and others like it did not totally integrate into it the blood collection phase—that is, a separate syringe still was required to collect the blood in a venipuncture step, and to transfer the blood to the device.

Yet another drawback with prior devices has been the inability to collect and dispense small amounts of serum from the same device that collects the whole blood. Although some devices have been described that do provide for serum separation and dispensing, generally these have been for fairly large amounts. Although the volume that is transferred in the device of U.S. Pat. No. 4,136,036 is only about 150 $\mu$l, such a device is useful only for skin puncture. Further, because a gel displacement method is used to decant the serum, large g forces (>2000 g's) are typically required, and many minutes (>10 min.), making such a device inconvenient for STAT medical situations. Still further, since a maximum quantity of 75 $\mu$l of serum is transferred to the larger volume dispensing devices, much of the volume of the serum stays on the large surface area of the large dispenser and thus is unavailable for dispensing. Yet, if the dispenser volume is decreased, there is a higher risk that air entrapment will occur when the serum is transferred to the smaller volume of the dispenser because of the uncontrollable nature of surface wetting. In this situation, dispensing would form air and liquid droplets, resulting in imprecise liquid dispensing.

Therefore, there has been a need prior to this invention to a) integrate all the functions of blood collection, separation and dispensing into a single article of manufacture so that whole blood from a vein enters one end, and serum is dispensed from another end, and b) to do this in a manner that permits smaller amounts of serum to be collected.

RELATED APPLICATIONS

In commonly owned U.S. application Ser. No. 442,826 filed by Columbus et al on Nov. 29, 1989, entitled "Blood Collection Device", there is described a phlebotomy device that has features similar to the instant invention, except that the second chamber into which serum is transferred, lacks the serpentine configuration of reduced volume as provided herein. In addition, the device is not permanently connected to a needle and a safety housing.

Commonly owned U.S. Ser. No. 484,014, filed by Columbus et al on Feb. 20, 1990 and entitled "Centrifuge-Containing Analyzer", refiled on an even date with this application as Ser. No. 527,797, discloses apparatus for dispensing separated serum from a second chamber of a phlebotomy device using an external source of air pressure. However, that second chamber lacks the features of this invention and the device is not integral with a needle and safety housing.

SUMMARY OF THE INVENTION

I have achieved the solution of the above-mentioned problems through the construction of an integrated device that includes as an integral part thereof, a needle, means to permit phase separation and transfer of serum, and the accurate dispensing of serum.

More specifically, in accord with one aspect of the invention, there is provided a multi-phase liquid collection, separation and dispensing device comprising a first chamber for collecting the liquid and for allowing the phases to separate under the influence of centrifugal force, a second chamber for receiving the lighter phase from the first chamber after phase separation, and means for fluidly connecting the chambers and including a valve operative in response to hydrostatic pressure from the light phase, the second chamber including an aperture constructed to permit transferred lighter phase to be removed. The device is improved in that it further includes a needle permanently and integrally connected to said first chamber, and housing means for protecting a user from being stuck by said needle when the needle is not being used to collect liquid, so that the device completely integrates the collecting function into one device.

In accord with another aspect of the invention, to achieve the dispensing of smaller volumes, there is provided a multi-phase liquid integral collection and separation device, comprising a first chamber for receiving the liquid and allowing the liquid to separate into at least two phases by spinning the chamber about an axis, and a second chamber and flow means allowing selective liquid flow of the lighter phase from the first chamber to the second chamber, the second chamber including a dispensing aperture, the flow means including a valve means for controlling flow between the chambers. The device is improved in that the second chamber has a volume no larger than about 150 $\mu$l, and is constructed to form a path extending in three dimensions from the flow means to the dispensing aperture, the sidewalls of the second chamber being spaced apart a distance no greater than that which provides a weak capillary effect to insure that liquid flow into the second chamber occurs without air entrapment.

In accord with still another aspect of the invention, there is provided a method for collecting whole blood, separating serum from the whole blood, and dispensing the separated serum. The method comprises the steps of:

a) exposing a needle permanently connected to a first, blood collecting chamber that is fluidly connected by a valve to a second, serum-collecting chamber having a dispensing aperture;

b) inserting the needle into a mammal so as to withdraw whole blood into the first chamber;

c) removing the needle from the mammal and withdrawing the needle into a protective housing in which the needle and the chamber are permanently mounted;

d) transferring the housing and chambers to a centrifuge;

e) spinning the centrifuge and its contents for a time and at a force sufficient to separate serum from cells in the blood-collecting chamber;

f) increasing the force after serum separation has occurred, to a value sufficient to open the valve by hydrostatic pressure of the serum, so that serum is transferred to the second chamber;

g) ceasing the spinning of step e) and removing the housing and the chambers from the centrifuge, and h) pressurizing the second chamber while maintaining the valve closed so as to dispense serum from the aperture.

In accord with still another aspect of the invention, there is provided a container for holding liquid and for allowing the liquid to be pressurized by pressurizing means to dispense the liquid from the container, the container including walls spaced apart to define a confining chamber, and means defining an aperture fluidly connecting the chamber with the atmosphere, the aperture being located in the chamber at a distance from the expected location of the liquid held in the chamber prior to it being pressurized. The container is improved in that the container further includes, at a predetermined location adjacent to the aperture, at least one protrusion extending from at least one of the defining walls, the protrusion extending out into the flow path of liquid being pushed to the aperture by the pressurizing means, a distance sufficient to create a resistance pressure detectable by a pressure transducer connected to the pressurizing means.

Therefore, it is an advantageous feature of the invention that a single integrated device provides a method of blood collection, serum separation, and presentation of serum for dispensing, without the need for any auxiliary apparatus other than a centrifuge and a source of compressed air.

It is another advantageous feature of the invention that such a device and method are provided for collection, transfer and dispensing of serum amounts no greater than 150 μl.

Other advantageous features will become apparent upon reference to the following Description of the Preferred Embodiments, when read in light of the attached drawings.

DESCRIPTION OF THE PREFERRED EMBODIMENTS

The invention is hereinafter described in connection with certain preferred embodiments, one of which provides that the phlebotomy tube is used to collect blood and is integral with the needle used to fill it, and is provided with a safety housing to prevent needle sticks, and mechanical means for maintaining phase separation of serum from blood cells (achieved by centrifuging). In addition, each of the various aspects and embodiments of the invention is useful regardless of whether the others are present, and it is useful whether or not the safety housing and the mechanical means for maintaining phase separation are included. In addition, it is useful on multi-phase liquids other than blood.

FIGS. 1-4 illustrate an improved phlebotomy tube 30 constructed in accord with one aspect of the invention, wherein a needle is not integral with the tube. The serum transfer chamber has been especially constructed to minimize the volume collected to no greater than 150 μl, while ensuring that no air entrapment occurs in that chamber. Thus, tube 30 is constructed with a chamber 32 for phase separation that has its long dimension l oriented perpendicular, not parallel, FIG. 2, to the direction of centrifugal force CF, arrow 34, and with a specially constructed valve 50. Chamber 32 is defined by a body member 33 having a blood intake end 36 and an opposite, serum-removal end 38. Chamber 32 extends from end 36 to delivery passageway 56. End 36 has an intake aperture 40 filled with a conventional septum 41, chamber 32 being either vented at 43 or evacuated due to attachment at 43 to an external vacuum source, to assist in blood intake. Aperture 40 allows entrance of whole blood via passageway 42 to chamber 32. The width "d" of chamber 32 is one of the shorter dimensions. Sidewall 44 of chamber 32 is the sidewall against which the heavier blood cells collect, whereas opposite sidewall 46 is adjacent the lighter serum fraction, during centrifugation. Thus, dimension "d" extends from the lighter phase into the heavier phase.

Figure 2:
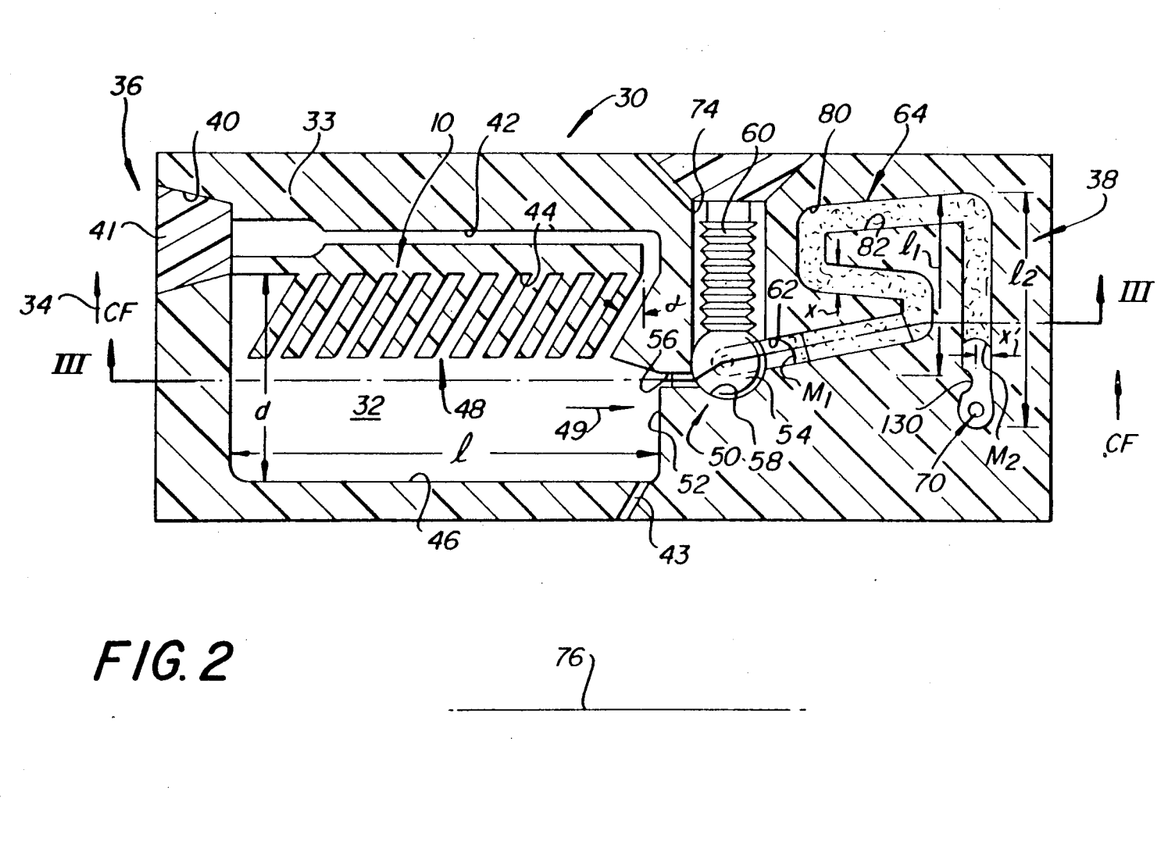
FIG. 2 is a section view taken generally along the line II of FIG. 3.

Optionally, fixed porous mechanical means, such as baffles 48, can be positioned along wall 44 so as to be disposed in the blood cells. As described in commonly owned U.S. application Ser. No. 325,725 filed on Mar. 20, 1989 entitled "Phase Separation Container with Fixed Means Preventing Remixing", such means act to retain the heavier phase from remixing when the lighter, serum phase is drawn off. The plates of the baffles are inclined at an angle alpha that resists remixing forces when flow occurs out of chamber 32 in the direction of arrow 49. Preferably, this angle is a value that is between about 30° and about 120°, most preferably about 60°. Preferably, the distance between the individual plates of baffles 48 is between about 0.018 cm and about 0.10 cm, most preferably about 0.025 cm. The thickness of each plate is not critical, so long as a significant number of such plates are present as will create the needed volume between them to collect the blood cells.

Alternatively, chemical agents can be used in place of baffles 48 to maintain the phase separation, for example cell agglutinating reagents.

Valve 50 is disposed at an end 52 of chamber 32 intermediate ends 36 and 38, positioned to draw off separated plasma or serum and lymphocytes. Importantly, valve 50 is constructed to open only in response to a hydraulic head of force, and not to the effects of force CF, regardless of the magnitude of the latter. To this end, valve 50 is preferably a ball check valve with a ball 54 positioned downstream of passageway 56 at chamber end 52. Ball 54 seats against a hemispherical seat 58, and is biased by a spring 60 aligned to act in a direction that is generally parallel to the direction of force CF. The spring constant of spring 60 is selected to ensure that ball 54 will act to move against spring 60 only in response to hydrostatic forces other than force CF.

A serum or plasma exit passageway 62 is constructed adjacent seat 58, to carry off the liquid when valve 50 opens. Passageway 62 joins a second chamber or compartment 64 defined by the same means as the chamber 32. This second chamber is sized to receive substantially all the serum that exits chamber 32 via valve 50. It is this second chamber that is especially constructed in accordance with the invention, as set forth hereinafter. It connects with two apertures—dispensing aperture 70 that is open to the atmosphere, and a pressurizing aperture 72, FIG. 1, that is temporarily sealed with a flangible seal 78. To avoid premature leakage of serum out of aperture 70, FIG. 2, that aperture is strategically located with respect to the meniscus of liquid that fills chamber 64 during transfer of serum through valve 50—it is downstream of meniscus $M_2$, as is readily achieved by locating aperture 70 closer to the spin axis 76 than is valve 50. In other words, distance $l_2$ is greater than distance $l_1$.

In accord with one aspect of the invention, chamber 64 is constructed to minimize serum volume so that it is less than 150 $\mu$l, and at the same time keep serum that is transferred to the chamber, free of entrapped air. To this end, sidewalls 80 and 82 of chamber 64 are spaced apart a distance x throughout the transverse passage of the liquid (as seen in FIG. 2), that will ensure a weak capillary effect is maintained. This capillary effect is that which ensures that, once force CF is reduced to zero, the menisci $M_1$ and $M_2$ remain in place during normal handling of device 30. Otherwise, air entrapment is likely to occur. Distance x can be varied between about 0.1 mm and about 2 mm. Beyond these values, the capillary effect is likely to be either too strong or too weak, respectively, to give desired performance. Most preferably it is about 1 mm.

Regarding the height of chamber 64, and its three-dimensional shape other than dimension "x", these are not as critical. As is more clearly shown in FIG. 3, chamber 64 preferably is ramped to have an increased height "h" as the path extends away from valve 50. This height is limited only by the volume of serum that can be expected to flow from chamber 32. The three-dimensional, winding shape of chamber 64 is dictated by the fact that this results from it being folded about itself. The folding is necessary to achieve a total path length "p", FIG. 1, that will also provide the desired volume for the expected volume of serum. It will be readily appreciated that other fold geometries, besides that shown, can also be used.

Spring 60 preferably sits in a trap 74, FIG. 2. The function of the trap is to collect the few red blood cells that will gather prior to and during centrifuging, in passageway 56, allowing only desired serum, or plasma and lymphocytes, to pass into chamber 64.

Device 30 can be assembled as two plates, using a foil layer (not shown) to achieve a seal that will allow a vacuum to be drawn using vent 43, as described above.

Such a device 30 can be spun in any convenient centrifuge, not shown, where the long dimension l is generally parallel to the spin axis 76. Preferred spin radii are about 2.5 cm, although a wide variety can be used.

The method of phase separating, using device 30, will be readily apparent from the preceding discussion. Whole blood is placed into chamber 32 by, e.g., a needle that penetrates septum 41. Device 30 is then spun about axis 76. However, the speed of rotation that is selected is slow—a speed producing no greater than 400 g's centrifugal force, and most preferably no greater than 30 g's. The reason is that device 30 is capable of achieving phase separation at such forces, using 2 mL of liquid, in less than 2 minutes, and in some cases less than 1 minute, due to the (relatively) short distance that the blood cells have to traverse to be separated. The serum, or plasma and lymphocytes, is separated in less than 1 minute if the centrifugal force is about 150 g's or greater, there being little separation time enhancement occurring at forces above 400 g's.

Once serum separation is achieved, a slight increase in force CF will produce, in the presence of a serum phase in chamber 32, an increased hydrostatic force in the direction of arrow 49. This in turn will produce a component force sufficient to overcome the spring constant of spring 60, so as to unseat the ball valve. Serum will thus flow into chamber 62 until there remains insufficient liquid (serum) to push against ball 54 and to cause liquid passage, and the valve closes. At this time, the menisci of the serum in chamber 64 will be at $M_1$ and $M_2$, thus leaving dispensing aperture 70 dry. In fact, the menisci remain at these locations even after force CF is reduced to zero, as the weak capillary attraction provided by side walls 80 and 82 will retain the liquid as shown. That is, the seal of the ball valve insures a vacuum is created to hold the column of serum in place.

Figure 1:
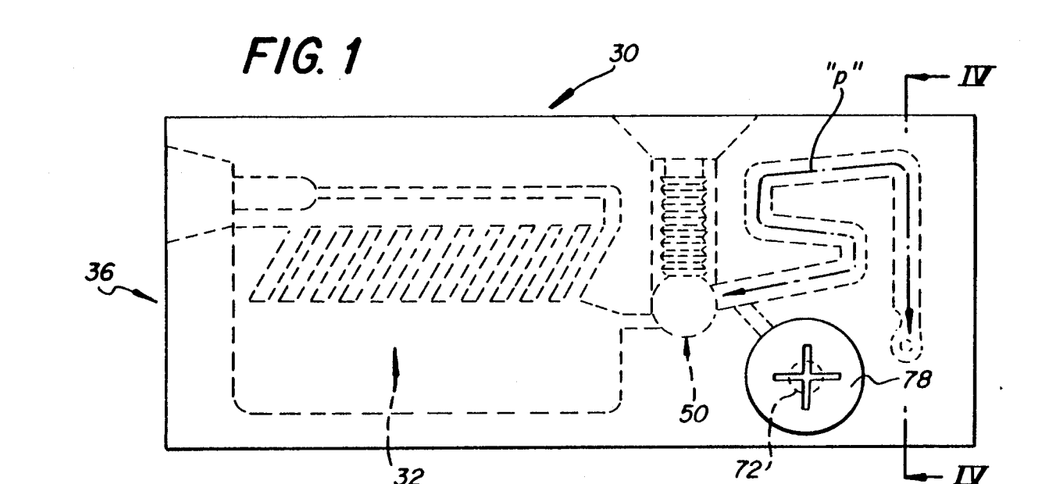
FIG. 1 is a plan view of a device prepared in accordance with one aspect of the invention.
Figure 4:
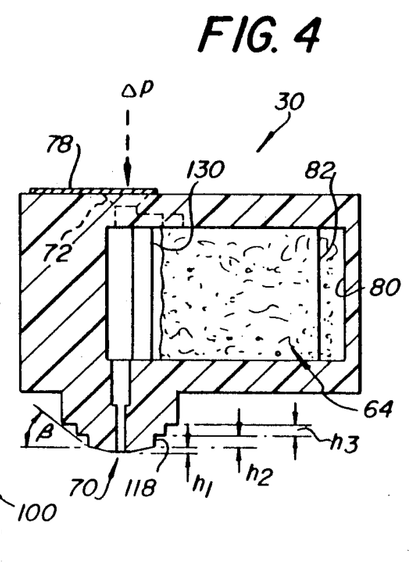
FIG. 4 is a section view of the device of FIG. 1 taken generally along the line IV—IV of FIG. 1 and showing in phantom the connection of the air pressure aperture with the second chamber.
Figure 13:
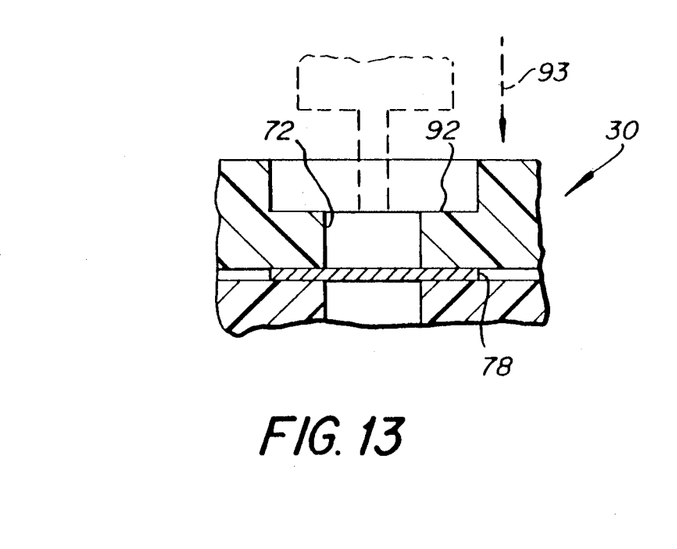
FIG. 13 is a fragmentary section view similar to that of FIG. 11, but of an alternate embodiment.

Thereafter, seal 78, FIGS. 1 and 4, is pierced by a source of compressed air, which can be any type, which applies a pressure $\Delta P$ to aperture 72, FIG. 4. This in turn is effective to dispense fractions of the serum out aperture 70. Alternatively, seal 78 can be inside device 30, FIG. 13, and the source of air pressure can be shaped to seat on a shoulder 92 of aperture 72, when it is brought down in the direction of arrow 93. This punctures seal 78.

For best results, aperture 70 has a nozzle with the following configuration:

The nozzle 100 surrounding aperture 70 can have any desired shape. Most preferably, it is the shape described and claimed in commonly-owned U.S. Ser. No. 310,151 filed on Feb. 14, 1989 entitled "Liquid-Controlling Nozzle Geometry for Dispensers of Liquids" now U.S. Pat. No. 4,971,763. More specifically, FIG. 3, nozzle 100 includes a bottom surface 101 extending a distance, preferably a radius $R_1$, from axis 106. Preferably surface 101 is an annulus. Useful values of $R_1$ are set forth hereinafter. However, surface 101 is joined directly at edge 110, with a surface 112 inclined at an angle $\alpha'$ to surface 101, the sign of angle $\alpha'$ being such as to cause surfaces 101 and 112 to form a convex surface. Surface 112 is generally annular and extends to subtend a distance, preferably a difference radius $R_2-R_1$, from axis 106. As used herein "generally annular" is satisfied if the shape approximates an annulus. In addition, nozzle 100 features a series of lands 114 and 116 stepped back along axis 106, up the side of the nozzle. Each of these lands is preferably generally annular in shape and generally parallel to surface 101 and has a dimension, preferably a radius $R_3$ and $R_4$, respectively, from axis 106, so that the surface area of each land is a function of the difference in the two bounding radii, $R_N - R_{N-1}$, where N is 3 for land 114, and N is 4 for land 116. Each land is stepped back, preferably straight back, so as to be spaced, along axis 106, a distance of $h_2$ and $h_3$, respectively, from the adjacent surface closer to surface 101, FIG. 4. (Distance $h_1$ for surface 262 is, of course, predetermined by the value of angle $\alpha$ and radii $R_1$ and $R_2$.)

An important feature of lands 114 and 116 is that their outermost radii $R_3$ and $R_4$, respectively, give to the exterior surface of nozzle 100, an overall angle $\beta$, FIG. 4, measured from the plane of surface 101, that is effective to give maximum drainage of liquid on the exterior of nozzle 100. Other important features are the recesses formed by the step in each land, and distances $h_2$ and $h_3$. That is, each step forms a gap in the overall cone shape suggested by angle $\beta$, with a step-back surface 118, FIG. 4, providing distance $h_2$ and $h_3$, such gaps being effective to trap and break up any sheaths of liquid that can be left on the exterior of nozzle 100.

The selection of angle beta, and of the distances $h_2$ and $h_3$ as noted above, is useful in nozzle 100 because accidental perfusion might occur and these features help insure that nozzle 100 will still dispense accurately as expected, in spite of perfusion.

Figure 3:
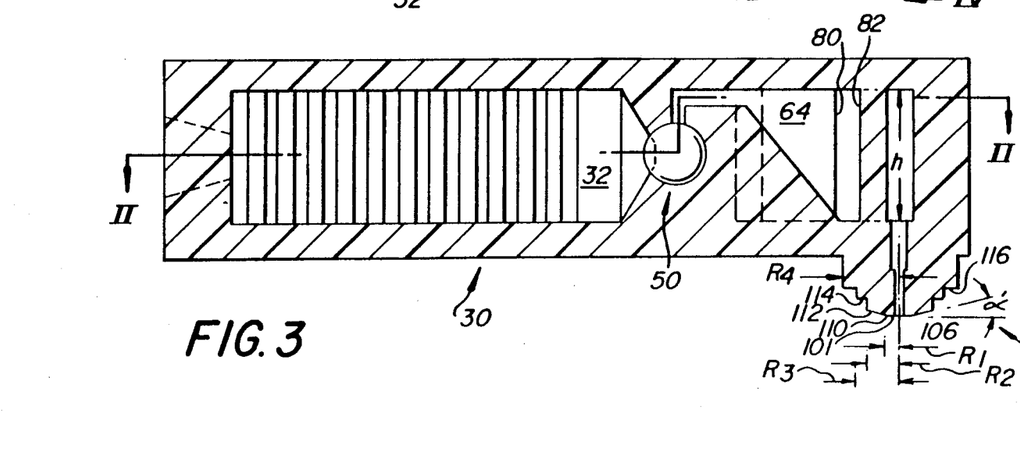
FIG. 3 is a section view taken generally along the line III—III of FIG. 2.

It will be recognized that the shape of lands 114 and 116, FIG. 3, need only be roughly angular, in which case $R_N - R_{N-1}$ is not strictly speaking determined by subtracting radii. In cases where $R_N$ and $R_{N-1}$ are dimensions of a non-circular curve, the value if $R_N - R_{N-1}$ is simply the width of that land as it extends around step-back surface 118, FIG. 4.

The following Table gives a list of preferred ranges, and of an exemplary "most preferred" value, for each of the aforementioned dimensions.

| Dimensional Values | | |
| --- | --- | --- |
| Items | Range | Most Preferred |
| Angle $\alpha$ | 6°–30° | 12° |
| Angle $\beta$ | 40°–60° | 53° |
| radius $R_1$ | 0.057–0.076 cm | 0.063 cm |
| radius difference ($R_2-R_1$) | 0.013–0.13 cm | 0.063 cm |
| radius difference ($R_3-R_2$) | 0.013–0.13 cm | 0.076 cm |
| radius difference ($R_4-R_3$) | 0.013–0.13 cm | 0.08 cm |
| height $h_2$ | 0.035–0.08 cm | 0.05 cm |
| height $h_3$ | 0.02–0.05 cm | 0.04 cm |

Most preferably, each of the edges created by the intersection of a surface such as land 114, 116 or surface 112, with the vertically-extending step-back surface 118, is relatively sharp, that is, has a radius of curvature not to exceed about 0.02 cm.

Because meniscus $M_2$ is not already at aperture 70 when dispensing is to start, it is desirable to provide means for detecting the presence of meniscus $M_2$ at some predetermined location along path "p" before it encounters the aperture. The reason is that patients' hemocrits vary from sample to sample. Hence, the exact location of meniscus $M_2$ at its upstream location (from aperture 70) cannot be predicted. As a result, the amount of pressurizing needed just to get meniscus $M_2$ to the aperture, is undetermined. The solution is readily achieved as follows:

A protrusion 130, FIG. 2, extends from at least one of walls 80 and 82, the full height of chamber 64, FIG. 4. This protrusion narrows the passageway of liquid flowing from meniscus $M_2$ to aperture 70, by an amount $(x - x^1)$ that produces a pressure increase when meniscus $M_2$ encounters it. To be detectable, the pressure increase need only be the amount of at least about 0.1 inch of water (0.025 kPa). The detection of such a pressure increase, due to the increased resistance, is readily achieved by a pressure transducer used with the pressurizing means (not shown). The exact amount of the extension of protrusion 130 depends upon the sensitivity of such pressure transducer. Preferably, the extension is about 0.025 cm. It can be as small as about 0.013 cm and as large as about 0.076 cm.

Alternatively, not shown, two opposing protrusions from both of the sidewalls can be used, in which case each protrusion extends only about one-half of $(x - x^1)$.

The shape of the protrusion 130 is not critical—it can be rounded or have a sharp corner.

The exact location of protrusion 130 along path "p" is also not crucial, so long as its location is known and represents a number of steps or half-steps of a pressurizing motor needed to move the meniscus $M_2$ from the protrusion to aperture 70. Preferably, protrusion 130 is adjacent aperture 70, and most preferably, closely adjacent as shown, FIG. 2.

Figure 5:
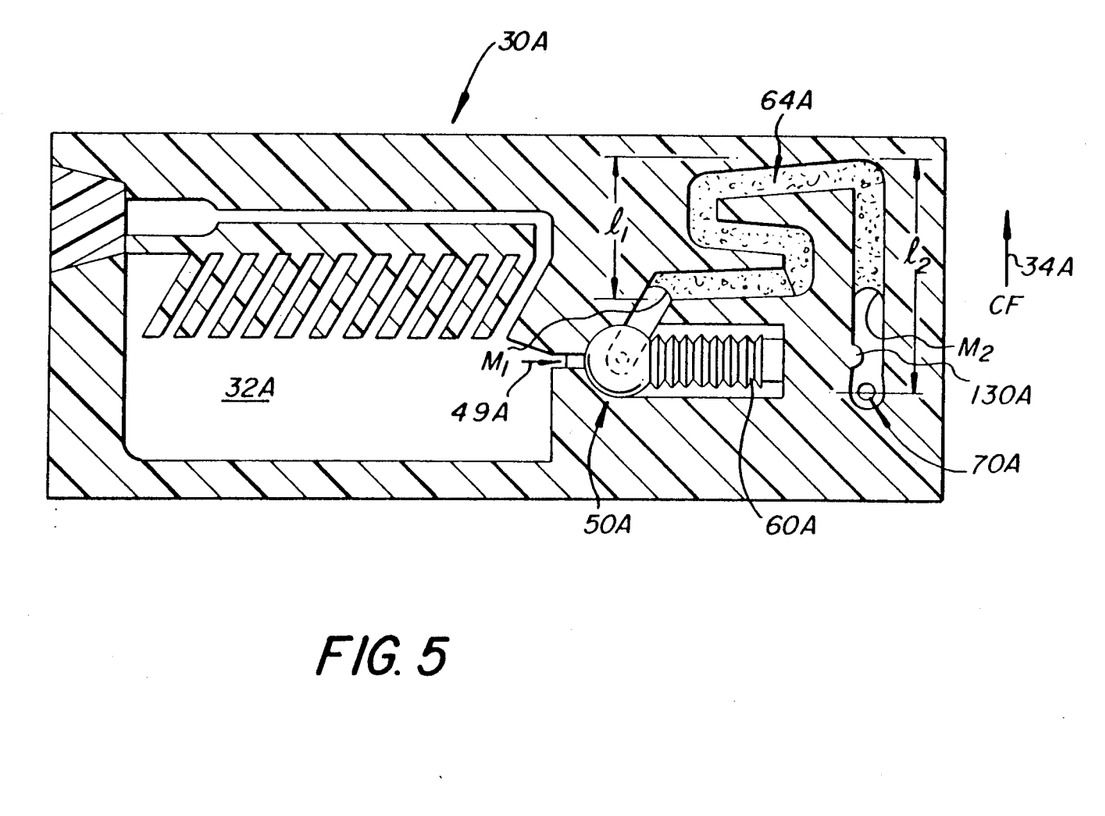
FIG. 5 is a section view similar to that of FIG. 2, but illustrating an alternate embodiment.

It is not essential that spring 60 be oriented to act parallel to the direction of force CF—it can alternatively be positioned to act in a perpendicular direction, FIG. 5. Parts similar to those previously described bear the same reference numeral, to which the distinguishing suffix "A" is appended.

Thus, device 30A is substantially identical to that previously described, having two chambers 32A and 64A, with a ball valve 50A between them, chamber 64A having a serpentine, three-dimensional folded shape that ends in a dispensing aperture 70A. However, unlike the previous embodiment, the valve of device 30A comprises a spring 60A oriented to act in a direction perpendicular to the direction 34A of force CF. Thus, valve 50A is clearly independent of the centrifugal force, no matter what its spring constant, and will respond only to the hydrostatic pressure created by serum pushing in the direction 49A. That in turn is achieved by increasing force CF beyond that used to separate serum from cells.

The above-described embodiments are temporarily connected to a phlebotomy syringe so that the inside end of the needle of the same (not shown) penetrates the septum at end 36, FIG. 1, to deliver whole blood. As is apparent, that needle is disconnected when the device 30 or 30A is removed and taken to a suitable centrifuge, which can be of any conventional construction, provided it delivers a spinning force CF in the direction shown.

Alternatively, in accord with another aspect of the invention, the device of the invention can be integrally mounted and attached to a needle, which in turn is an integral part of a device that includes a safety housing, FIGS. 6–12. Parts similar to those previously described bear the same reference numeral, to which the distinguishing suffix B is appended.

Figures 6, 8:
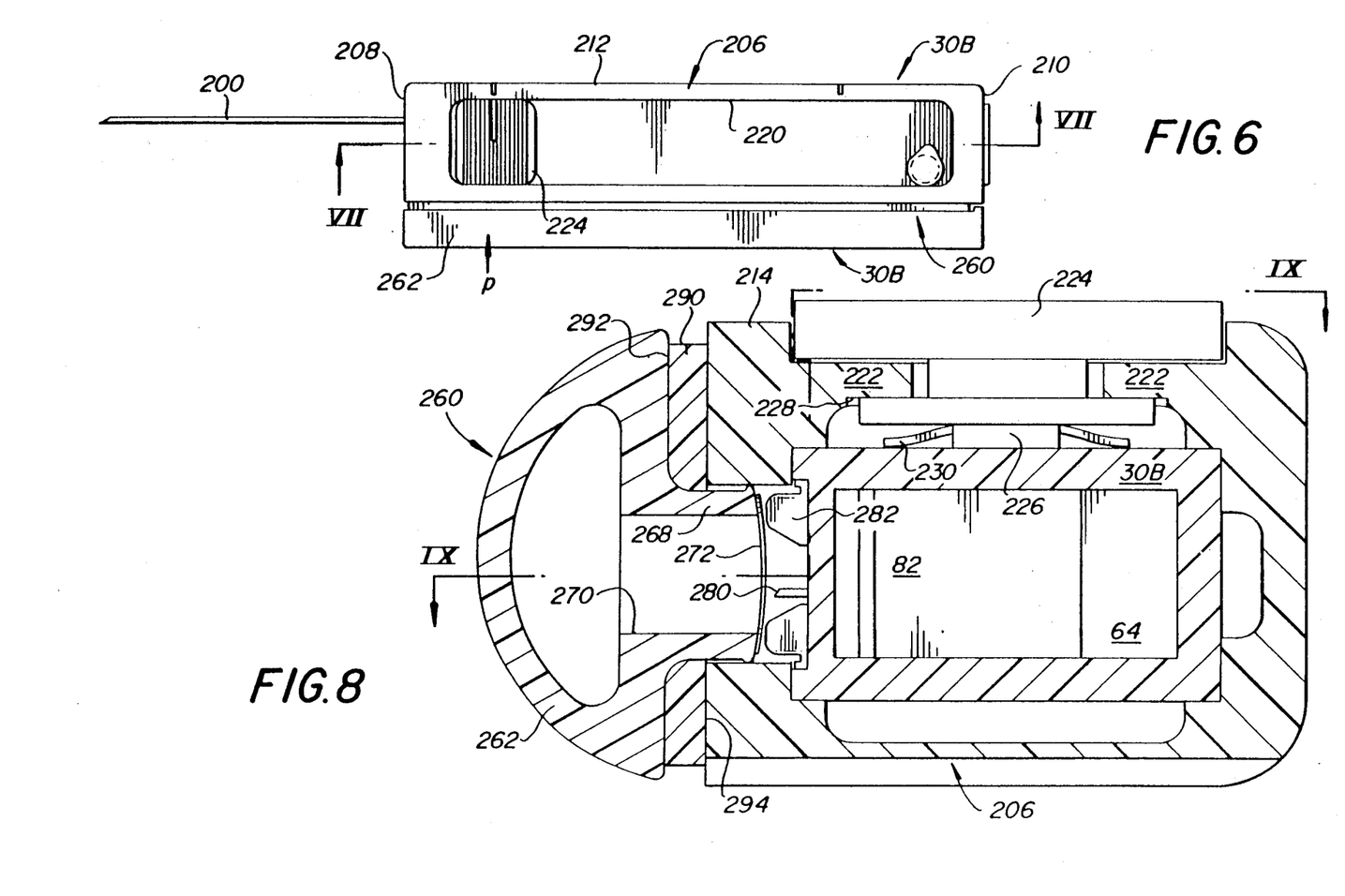
FIG. 6 is a plan view of a combination of a needle and needle sheathing housing and a device of FIG. 2 within the housing, an alternative embodiment, illustrating the "in use" configuration.
FIG. 8 is a section view taken generally along the line VIII—VIII of FIG. 7.
Figure 7:
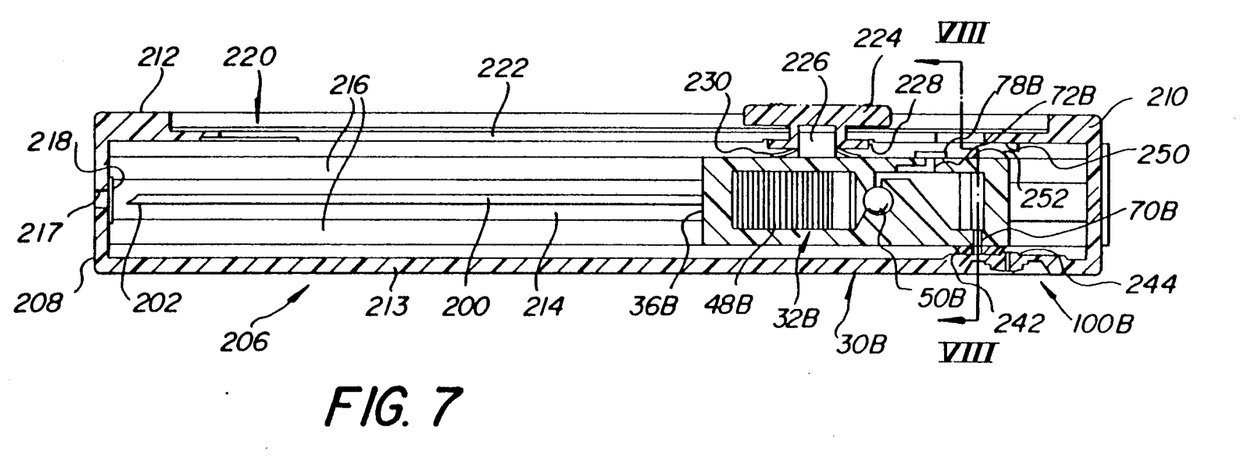
FIG. 7 is a section view taken generally along line VII—VII of FIG. 6.
Figure 9:
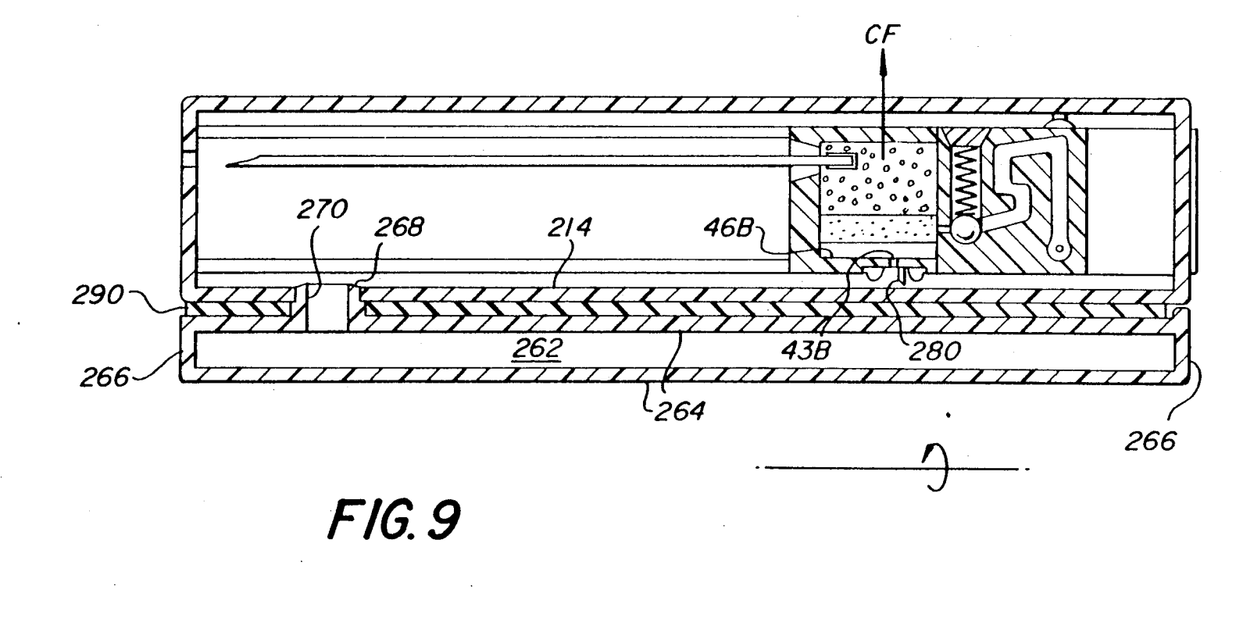
FIG. 9 is a section view taken generally along the line IX—IX of FIG. 8.

Thus, FIG. 6, device 30B is provided as described above, for collecting whole blood in chamber 32B, FIG. 7, and passing separated serum through valve 50B into chamber 64B, which has an air pressure inlet 72B covered by a seal 78B, and a dispensing aperture 70B. Appropriate means such as baffle plates 48B are included to maintain phase separation.

However, unlike the previous embodiments, a needle 200 is permanently attached to device 30B at end 36B, to provide blood when the needle is injected into a mammal. Because end 202 of such a needle, if left exposed, is a threat to those handling it, both the needle and device 30B are slidably mounted in a safety housing 206 having a frame comprising end walls 208 and 210, a top wall 212, a bottom wall 213 and side walls 214. Rails 216 are provided for device 30B to slide between, on sidewalls 214. End wall 208 is provided with an aperture 217 with a temporary seal 218, that will allow needle 200 to be pushed through when it is to be injected into a mammal. To allow device 30B and its needle 200 to be moved relative to housing 206, a slot 220 is formed in top wall 212. The slot has opposed shoulders 222, FIG. 8, that slidably accommodates a manual button 224 mounted on a post 226 projecting from device 30B, FIG. 6. Optionally, shoulders 222 have a recess 228 into which button 224 removably snaps by the action of a leaf spring 230, to releasably hold device 30B as shown in FIGS. 7 and 8 for shipment to a user.

Also unlike the previous embodiments, several other features are provided on housing 206. Dispensing nozzle 100B incorporates on housing 206 all the features of nozzle 100 that were on device 30 or 30A previously described, and matching bosses 242 and 244 are provided on device 30B at aperture 70B, and on bottom wall 213 opposite nozzle 100B, to allow aperture 70B to properly seal with nozzle 100B as described hereinafter. Additionally, a locking finger 250 projects from the inside of top wall 212 near end wall 210, to cooperate with a rounded locking detent 252 on device 30B when aperture 70B seals to nozzle 100B.

Preferably, means 260 are also permanently and integrally included with device 30B to provide a source of partial vacuum for chamber 32B. Most preferably, such means comprise a container 262 defined by side walls 264 and 266, FIG. 9, one of side walls 264 having a boss 268, FIGS. 8 and 9, facing towards and projecting through one of the sidewalls 214 of housing 206. Boss 268 is in turn provided with a draw aperture 270 that is temporarily sealed with a foil 272, FIG. 8, adequate to retain a partial vacuum in container 262, as is well known. For best results, container 262 comprises a plastic which is polyethylene terephthalate, or any of the polymers described in *Research Disclosure*, published by Emsworth Studios, 260 West 39 Street, New York, N.Y. 10018, Nos. 29416 and 29484, in the October, 1988 issue. More specifically, the latter include blends of poly(ethylene 2,6-naphthalenedicarboxylate) or its co-polyester, with from 1 to 30 weight percent of poly(ethylene-co-vinyl alcohol). These blends demonstrate a low degree of gas permeability, so that the blends are unusually effective in holding partial vacuum during storage.

To cooperate with boss 268, means are provided on device 30B to puncture seal 272 and to fluidly connect chamber 32B with the vacuum of container 262. More specifically, aperture 43B in sidewall 46B of device 32B has mounted adjacent thereto, FIGS. 8 and 9, both a prick 280 and a sealing shoulder 282 surrounding aperture 43B. Shoulder 282, FIG. 8, seals against boss 268 when the boss and aperture 43B are aligned and pushed together. Such alignment occurs when the needle 200 is fully projected out of housing 206, FIG. 6.

To bias container 262 away from prick 280 until liquid collection is desired, container 262 is attached to device 30B via a compressible foam layer 290, FIG. 8, preferably provided with adhesive on both its surfaces 292 and 294 for securing container 262 and housing 206 together. The biasing by layer 290 is then readily overcome by finger pressure P, FIG. 6, to cause prick 280 to penetrate seal 272 and shoulder 282 to seal against boss 268.

Optionally, container 262 can be omitted, and instead, an external vacuum source can be connected to aperture 43B. However, container 262 is preferred as it renders device 30B self-contained.

Figure 10:
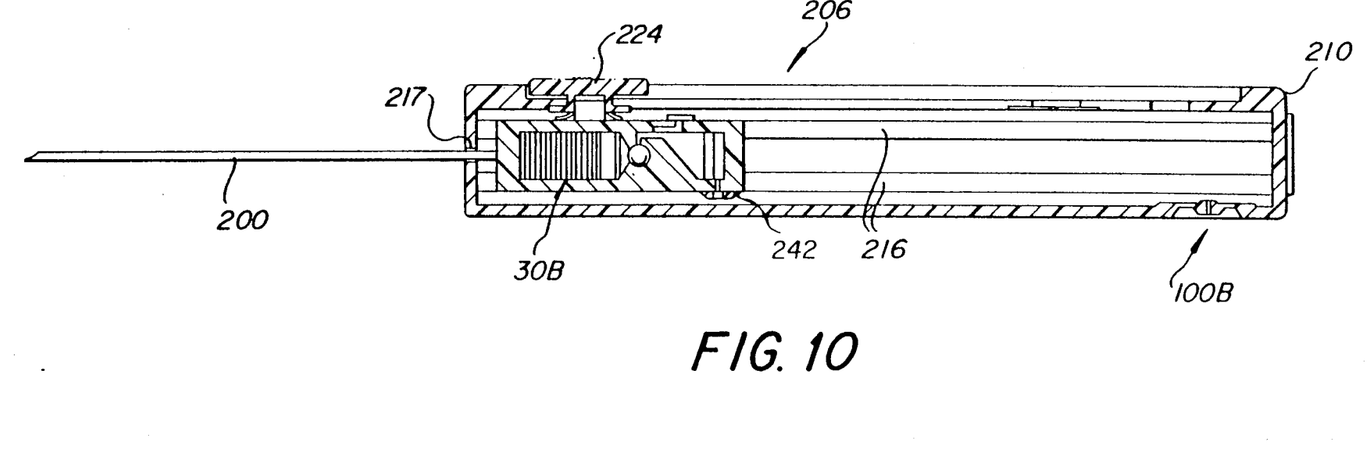
FIG. 10 is a section view similar to that of FIG. 7, but in the configuration with the needle fully extended as shown in FIG. 6.
Figure 11:
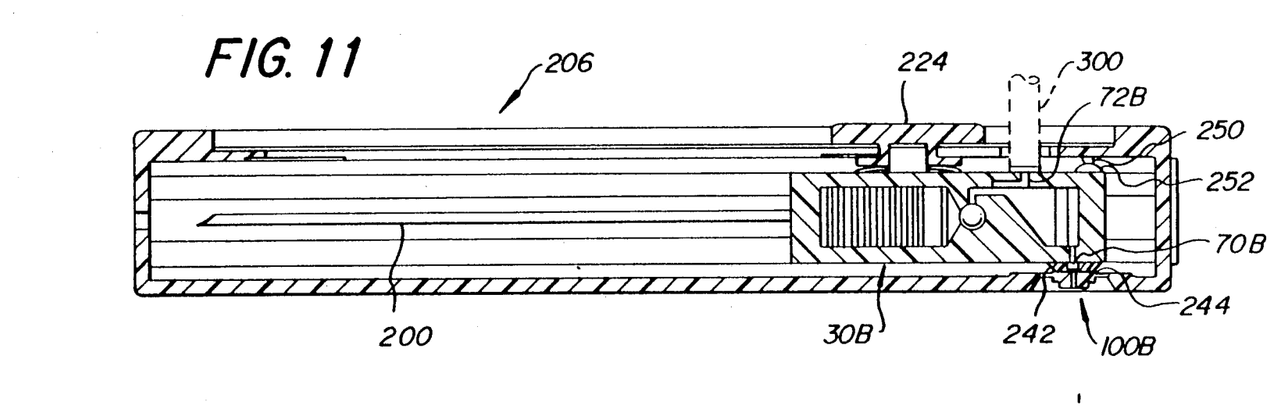
FIG. 11 is a section view similar to that of FIG. 7, but with the device in the locked metering position.
Figure 12:
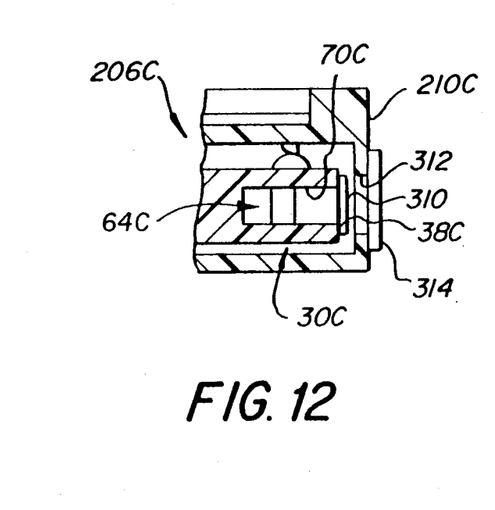
FIG. 12 is a fragmentary sectional view similar to that of FIG. 11, but illustrating a second chamber of a different embodiment, wherein a pipette rather than external air pressure is used to extract the separated lighter phase.

To activate device 30B for use, button 224 is simply depressed to unseat it from recess 228, and device 30B is slid within housing 206 until needle 200 is fully extended out through aperture 217, FIGS. 6 and 10. The entire device is then injected into the mammal to collect blood, while pressure P is applied to container 262, FIG. 6. Thereafter, the needle and device 30B are withdrawn by moving button 224 back, FIG. 11, until locks 250 and 252 are engaged and bosses 240 and 242 are sealed together. At this point, device 30B is permanently positioned in housing 206, and it is inserted into an appropriate centrifuge which applies a centrifugal force CF, FIG. 9. Serum separation and transfer occur as described for the embodiments of FIGS. 1–4. Thereafter, a source 300 of compressed air, shown in phantom, FIG. 11, is brought into contact with aperture 72B, preferably by penetrating seal 74B, FIG. 7, and the separated serum is dispensed through aperture 70B and nozzle 100B.

Thus, the only apparatus not provided for in the integrated device, needed for blood collection, separation and dispensing, are the centrifuge and the source of air pressure, both of which are conventional items.

Alternatively, it is not necessary that dispensing of the separated serum occur through the use of a ΔP pressure impulse from a source 300 to dispense out through nozzle 100B. Instead, the integrated device 30B (that includes housing 206) can provide for removal of serum using a pipette, FIG. 12. Parts similar to those previously described bear the same reference numeral, to which the distinguishing suffix "C" is appended.

Thus, device 30C and its safety housing 206C are constructed as described for FIGS. 6–11, except for chamber 64C and end wall 210C of housing 206C. That is, chamber 64C has an aperture 70C that is greatly enlarged, and is located in end wall 38C, with a temporary seal 310. (The serpentine path of chamber 64C is otherwise generally the same as described before.) In addition, end wall 210C has an aperture 312 sized similarly to aperture 70C, sealed by seal 314. That is, both apertures 70C and 312 are large enough to permit passage of a conventional pipette through the seals and sufficiently far into chamber 64C as to allow aspiration removal of serum from device 30C.

The invention has been described in detail with particular reference to preferred embodiments thereof, but it will be understood that variations and modifications can be effected within the spirit and scope of the invention.

What is claimed is:

1. In an integral multi-phase liquid collection and separation device, comprising a first chamber containing a partial vacuum for drawing in the liquid and allowing the liquid to separate into at least two phases by spinning the chamber about an axis, and a second chamber and flow means allowing selective liquid flow of the lighter phase from said first chamber to said second chamber, said second chamber including a dispensing aperture, said flow means including a valve means for controlling flow between said chambers and having a predetermined bias to close off flow out of said first chamber at all times;

the improvement wherein said second chamber has a volume no larger than about 150 µl, and is constructed to form a path extending in three dimensions from said flow means to said dispensing aperture, the sidewalls of said second chamber being spaced apart a distance no greater than that which provides a weak capillary effect, to insure that liquid flow into said second chamber occurs when said valve means bias is overcome, without air entrapment.

2. A device as defined in claim 1, wherein said sidewall spacing is between about 0.1 mm and about 2 mm for said entire path length.

3. A device as defined in claim 1, and further including pressure-generating means comprising a protrusion extending into the flow path of liquid in said second chamber, a distance sufficient to create a change in pressure of liquid of at least 0.025 kPa.

4. In an integral multi-phase liquid collection, separation and dispensing device comprising means defining a first chamber for collecting the liquid and for allowing the phases to be separated under the influence of centrifugal force, said means additionally defining a second chamber connected to said first chamber for receiving the lighter phase from said first chamber after phase separation, and means for fluidly connecting said chambers and including a valve operative to allow transfer of said lighter phase, said second chamber including an aperture constructed to permit transferred lighter phase to be removed;

the improvement wherein said device further includes a needle permanently and integrally connected to said first chamber means, and permanently associated housing means mounting said needle for alternately exposing said needle and for surrounding said needle so as to protect a user from being stuck by said needle when the needle is not being used to collect liquid, so that the device completely integrates the collecting function into one device.

5. A device as defined in claim 4, wherein said second chamber has a volume no larger than about 150 µl, and is constructed to form a path extending in three dimensions from said flow means to said dispensing aperture, the sidewalls of said second chamber being spaced close enough together to insure that liquid flow into said second chamber occurs without air entrapment.

6. A device as defined in claim 4, wherein said sidewall spacing is no greater than that which provides a weak capillary effect.

7. A device as defined in claim 4, 5 or 6, wherein said sidewall spacing is between about 0.1 mm and about 2 mm for said entire path length.

8. A device as defined in claim 1 or 4, and further including in said first chamber, means for maintaining phase separation after spinning.

9. A device as defined in claim 4, and further including liquid-drawing means permanently and integrally attached to said housing means, for providing a partial vacuum to said first chamber to assist in blood collection in said first chamber.

10. A device as defined in claim 9, wherein said liquid-drawing means comprise a container in which a partial vacuum has been previously created, said container including a draw aperture and a temporary seal over said aperture adequate to retain said vacuum, and further including means for penetrating said temporary seal on demand and for connecting said draw aperture and said first chamber together so that said partial vacuum is effective in said first chamber to draw in liquid.

11. A device as defined in claim 10, and further including bias means between said container and said housing means for temporarily spacing said penetrating means from said seal.

12. In an integral multi-phase liquid collection and separation device, comprising a first chamber for receiving the liquid and allowing the liquid to separate into at least two phases by spinning the chamber about an axis, and a second chamber and flow means allowing selective liquid flow of the lighter phase from said first chamber to said second chamber, said second chamber including a dispensing aperture, said flow means including a valve means for controlling flow between said chambers;

the improvement wherein said second chamber has a volume no larger than about 150 µl, and is constructed to form a path extending in three dimensions from said flow means to said dispensing aperture, the sidewalls of said second chamber being spaced apart a distance no greater than that which provides a weak capillary effect, to insure that liquid flow into said second chamber occurs without air entrapment; and further including in said second chamber at a predetermined location adjacent to said aperture, means for generating a pressure change indicative of the presence of liquid advancing towards said aperture.

13. A method for collecting whole blood, separating serum from the whole blood, and dispensing the separated serum, the method comprising the steps of
a) exposing a needle permanently connected to a first, blood-collecting chamber that is fluidly connected by a valve to a second, serum-collecting chamber having a dispensing aperture;
b) inserting the exposed needle into a mammal so as to withdraw whole blood into said first chamber;
c) removing said needle from the mammal and withdrawing said needle into a protective housing in which said needle and said chamber are permanently mounted;
d) transferring said housing and chambers to a centrifuge;

e) spinning the centrifuge and its contents for a time and at a force sufficient to separate serum from cells in said blood-collecting chamber;

f) increasing said force after serum separation has occurred, to a value sufficient to open said valve by hydrostatic pressure of the serum so that serum is transferred to said second chamber;

g) ceasing the spinning of step e) and removing said housing and said chambers from the centrifuge, and h) pressurizing said second chamber while maintaining said valve closed so as to dispense serum from said aperture.

14. In a multi-phase liquid collection, separation and dispensing device comprising a first chamber for collecting the liquid and for allowing the phases to be separated under the influence of centrifugal force, a second chamber for receiving the lighter phase from said first chamber after phase separation, and means for fluidly connecting said chambers and including a valve operative to allow transfer of said lighter phase, said second chamber including an aperture constructed to permit transferred lighter phase to be removed;

the improvement wherein said device further includes a needle permanently and integrally connected to said first chamber, and housing means for protecting a user from being stuck by said needle when the needle is not being used to collect liquid, so that the device completely integrates the collecting function into one device, and further including in said second chamber at a predetermined location adjacent to said aperture, means for generating a pressure change indicative of the presence of liquid advancing towards said aperture.

* * * * *